US005656651A

United States Patent [19]
Sovak et al.

[11] Patent Number: 5,656,651
[45] Date of Patent: Aug. 12, 1997

[54] ANDROGENIC DIRECTED COMPOSITIONS

[75] Inventors: Milos Sovak, La Jolla; Jerome C. Bressi; James Gordon Douglass, III, both of San Diego; Brian Campion, Solana Beach; Wolfgang Wrasidlo, La Jolla, all of Calif.

[73] Assignee: Biophysica Inc., La Jolla, Calif.

[21] Appl. No.: 491,130

[22] Filed: Jun. 16, 1995

[51] Int. Cl.$^6$ ............... A61K 31/415; C07D 233/72; C07D 233/86; C07D 233/84; C07D 233/88; C07D 405/04

[52] U.S. Cl. ............... 514/396; 514/397; 514/398; 514/399; 514/400; 514/391; 548/320.1; 548/321.1

[58] Field of Search ............... 514/396–400, 514/391; 548/320.1

[56] References Cited

U.S. PATENT DOCUMENTS

| | | | |
|---|---|---|---|
| 4,097,578 | 6/1978 | Perronnet et al. | 424/273 R |
| 5,084,472 | 1/1992 | Moguilewsky et al. | 514/389 |
| 5,166,358 | 11/1992 | Seuron et al. | 548/321.1 |
| 5,411,981 | 5/1995 | Gaillard-Kelly et al. | 514/386 |

FOREIGN PATENT DOCUMENTS

| | | | |
|---|---|---|---|
| 0 436 426 B1 | 7/1991 | European Pat. Off. | 540/316.4 |
| 0 494 819 A1 | 7/1992 | European Pat. Off. | 548/316.4 |
| 0 580 459 A1 | 1/1994 | European Pat. Off. | 54/316.4 |

OTHER PUBLICATIONS

Moguilewsky et al., III "Pharmacological and Clinical Studies of The Antiandrogen Anandron", J. Steroid Biochem (1987), 27:871–875.

Battmann et al., "RU 58841, A New Specific Topical Antiandrogen: A Candidate of Choice for the Treatment of Acne, Androgenetic Alopecia and Hirsutism", J. Steroid Biochem. Molec. Biol. (1994), 48:55–60.

Neumann and Topert, "Pharmacology of Antiandrogens", J. Steroid Biochem. (1986), 25:885–895.

Rasmusson and Toney, "Therapeutic Control of Androgen Action", Annual Reports in Medicinal Chemistry (1994), 225–234.

Teutsch et al., "Non–Steroidal Antiandrogens: Synthesis and Biological Profile of High–Affinity Ligands for the Androgen Receptor", F. Steroid Biochem. Molec. Biol. (1994), 48:111–119.

Primary Examiner—Floyd D. Higel
Attorney, Agent, or Firm—Flehr Hohbach Test Albritton & Herbert LLP

[57] ABSTRACT

Substituted phenylthiohydantoins are provided for use in detecting the presence of tumor cells having androgenic receptors and providing for cytostatic and cytotoxic activity toward such cells. The subject compounds provide for vehicles for specific targeting to the androgenic receptor containing cells of cytostatic and/or cytotoxic agents, heavy or light radioactive or radioopaque atoms, and the like for detection and treatment of cancer cells involving androgenic receptors or blocking androgenic receptors.

7 Claims, No Drawings

ANDROGENIC DIRECTED COMPOSITIONS

INTRODUCTION

TECHNICAL FIELD

The field of this invention is diagnosis and treatment of androgenic related neoplasia and blockage of androgenic receptors.

BACKGROUND

The growth of prostate cancer (CaP) depends upon the presence of androgen (male) hormones, acting via androgen receptors contained in the cell's nucleus. The only effective, albeit temporary, therapy of prostate cancer is based upon interference of male hormone production or activity, using estrogenic steroids or non-steroidal substances to block the cancer cells' androgen receptors. There are a number of problems with these therapies. Steroidal estrogens had to be abandoned due to their high cardiovascular toxicity. The only steroidal compound clinically used today is cyproterone acetate. However, it also binds to the glucocorticoid and progestin receptors. Current, clinically-used non-steroidal anti-androgens such as Flutamide, Casodex or Anandron do not bind sufficiently to androgen receptors to achieve their complete blockage. None of the current anti-androgens provide permanent relief. It is suspected that the incomplete blockage of the receptors may be the reason why, with time, the therapy invariably becomes ineffective as the CaP cells mutate having proliferated metastatically. At that phase, the cells cannot be substantially influenced by any known chemotherapy or radiation.

There is the further consideration that the current armamentarium for the diagnostic staging of prostate cancer is extremely poor and yet essential in choosing the therapeutic mode. Proof of metastatic dissemination beyond the prostate excludes surgery and relegates these patients to systemic therapy. With improved diagnostic staging, unnecessary prostatectomies, a major and potentially mutilating surgery, could be avoided.

Only recently, an assay has become available for the detection of CaP cells circulating in the blood. However, that finding alone does not imply the existence of metastases. Typically, early metastases occur in the lymph nodes and the later ones develop in the bones. While $^{99}$Tc scans can visualize bone defects, the lymph node metastases are extremely difficult to locate since typically, the infiltrated nodes are neither enlarged nor show changes on either magnetic resonance or x-ray computed tomography. Further, because of their low metabolic rate, the pathological nodes cannot be identified by positron emission spectrography using $^{18}$F-deoxyglucose. Lymph node biopsy is possible only in the pelvic area. Early metastases in inaccessible paraaortic lymph nodes cannot be detected and consequently these patients are operated upon needlessly. Recently developed radiolabeled monoclonal antibodies against prostate cancer have only a limited use due to their low target specificity and long persistence in the blood pool, liver and spleen, which interferes with the imaging.

There have been a number of attempts to develop a CaP radionuclide scanning agent. Several radioiodinated androgen steroids were made, but they suffer from synthetic complexity. Steroidal androgens labeled with $^{18}$F were synthesized as a potential PET imaging agent for prostate cancer, but their practicability is limited due to the complicated synthesis and need for specialized rare equipment (PET scanners) to detect positron emitting radionuclides. There is a further consideration that androgens promote CaP growth.

There is, therefore, substantial interest in developing novel compounds which can provide for the diagnosis and therapy of prostate cancer.

Relevant Literature

N-aryl substituted imidazolinediones have been reported in DE32 22 523; Offenlegungsschrift 26 49 925; WO88/03404; EP0 436426; EP0 494819; EP0 580459, and Teutsch, J. Steroid Biochem. Molec. Biol. (1994) 48:111-119. The activity of the trifluoromethyl, nitro- and trifluoromethyl, cyanophenyl derivatives as high-affinity ligands for the androgen receptor are reported in Teutsch, supra., as well as in many of the foregoing patents.

SUMMARY OF THE INVENTION

Specific N-substituted 3-trifluoromethyl-4-cyano phenylthio-4',4'-dimethylhydantoins, their amino and thione analogs are provided having substitution at the remaining annular atom. Substituents include cyclic and aliphatic groups. Of particular interest are groups which can be used for imaging and/or have enhanced therapeutic index.

DESCRIPTION OF THE SPECIFIC EMBODIMENTS

N-substituted arylthio-4',4'-dimethylhydantoins are provided, where when the 3-N-substituent comprises other than an iodoaryl group, the hydantoin is a monothiohydantoin, where the other $sp^2$ carbon atom is bonded to oxygen, or nitrogen (imino). The compounds find use for diagnosis and/or therapy associated with androgenic receptors. The subject compounds have high affinity for androgen receptors of a variety of cell types and are able to exert at least one of proliferation inhibition or cytotoxicity for therapy or preferential binding for use as a detection medium for cells and tissues comprising androgenic receptors or for other identification.

For the most part, the subject compositions can be divided into three categories as characterized by the N-substituent: A group of from two to eight, usually from two to six carbon atoms, more usually from two to four carbon atoms, particularly two to three carbon atoms, which may be aliphatic or heterocyclic, generally having from zero to three, more usually from zero to two heteroatoms, preferably from one to two heteroatoms, which may be derivatized, particularly alkylated or acylated, where the alkyl or acyl group will be of from one to ten, more usually one to eight, preferably of from one to six carbon atoms, where the acyl group will generally be of from two to six carbon atoms, where the non-oxo-carbonyl may be bonded to from zero to two oxygen and/or nitrogen atoms, and zero to one carbon atoms; where the heterocycle will be from five to six annular members, particularly five annular members, where the annular members will be oxygen and nitrogen, generally having from 1 to 3 annular heteroatoms; the second group will have an agent, frequently a cytotoxic agent and/or imaging agent bonded to the hydantoin, normally through a linking group of from one to six, usually one to four carbon atoms, preferably two to three carbon atoms and one heteroatom, where the linking group may include one or more functionalities, such as amino, oxy, and non-oxo-carbonyl, where amides and esters may be involved, e.g. urethanes; and the third group will involve carbocyclic aryl groups, particularly iodoaryl, which may be bonded to the nitrogen of the hydantoin through a linking group of from one to eight, usually two to six carbon atoms, preferably two to three carbon atoms, where the linking group may include an amino, oxy or non-oxo-carbonyl functionality, particularly ester or amide, and the aryl group may be substituted with oxy, amino, non-oxo-carbonyl, and derivatives thereof. As the aryl group, phenyl is of particular interest.

Tissue comprising cells with androgen receptors include prostate tissue, ovary tissue, testes, etc. Hosts of interest include primates, e.g. humans, domestic animals and pets.

The first group of the compounds of the subject invention will have the following formula:

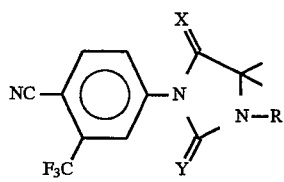

wherein:

X is oxygen or nitrogen, where the proviso that when R is iodoaryl, X may be sulfur;

Y is sulphur, with the proviso that when R is iodoaryl group, Y may be sulphur, oxygen or nitrogen, preferably X and Y are different;

R is an organic group, which may be aliphatic, alicyclic, aromatic, heterocyclic, or combinations thereof, to be further defined below.

The first group of compounds will comprise monothiohydantoins, where the other oxo group of the hydantoin will be oxygen or nitrogen. These groups will, for the most part, have R having the following formula

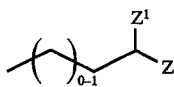

wherein:

Z is hydroxyl, amino, a substituted amino or a 4-diazolyl, particularly a 4-(1',3'-imidazolyl);

$Z^1$ is hydrogen, hydroxyl, or may be taken together with Z to provide for olefinic or acetylenic unsaturation, or a 2,2-dimethyldioxalane.

The substituents on amino nitrogen may be varied widely, depending upon the use of the compound. For cytotoxicity or antiproliferative activity, the amino group may be unsubstituted or substituted, particularly with the single acyl group, where the acyl group may serve to enhance the activity of the compound by changing its pharmacokinetic activities, by providing for a second cytotoxic or antiproliferative compound, by providing for a chelating agent for chelating a metal ion, particularly a radioactive metal or non-metallic on, for carrying a radioopaque atom, or the like. Radioactive elements include fluorine, iodine, gadolinium, technetium, etc.

Similarly, the hydroxyl, particularly the terminal hydroxyl, may be employed as a site for linking, forming ethers or esters, where the groups bound to oxygen will come within the above description.

In addition, iodoaryl groups may be employed which are linked to the nitrogen through an alkyl chain, where the alkyl chain may be of from 1 to 6, usually from 1 to 4, preferably from 2 to 4 carbon atoms. The iiodoaryl group may be linked directly to the carbon of the alkyl group or linked through a heteroatom, particularly nitrogen or oxygen, e.g. amide, secondary amine, ether, ester, etc. where the iodoaryl group may have a non-oxo-carbonyl or amino group linked to an annular carbon atom as part of the linking chain. The iodoaryl will generally have from 2 to 4, usually 2 to 3 iodine atoms, and may be further substituted with oxy, particularly hydroxy or alkoxy of from 1 to 3 carbon atoms, or amino, or a substituted amino (mono- or disubstituted), having alkyl substituents having a total of 1 to 6 carbon atoms, more usually 1 to 4 carbon atoms, and 0 to n-1 oxy groups, where n is the number of carbon atoms in the substituent. A variety of aminosubstituted symmetrically substituted triiodoisophthaldiamides and diaminosubstituted symmetrically substituted triiodobenzamides have been reported in the literature, where the nitrogen atoms are substituted with acyl groups, alkyl groups or oxyalkyl groups of 1 to 6, usually 1 to 4 carbon atoms and 0 to n-1 oxy groups. See, for example, U.S. Pat. Nos. 4,547,357; 4,021,481; 4,364,921 and 4,341,756 and references cited therein. The carboxyl group may be used to link the iodoaryl group to the thiohydantoin throgh the alkyl chain.

Illustrative R groups include: allyl, propynyl, aminoethyl, aminopropyl, 2-hydroxypropyl, 3-hydroxypropyl, 2-hydroxyethyl, 2,3-dihydroxypropyl, 2-hydroxy-3-acetoxypropyl, 4-benzamidobutyl, 4-fluorobutyl, 4-iodobut-3-enyl, 3-(4'-oxazolyl-1,3)propyl, 2-(4'-diazolyl)ethyl, 3-(propionamido)propyl, N-phenoxycarbonyl 2-aminoethyl, N-methoxycarbonyl 2-aminoethyl, 3-(3',5'-diiodo-4'-dimethylaminophenyl)propyl, 2-(3',4',5'-triiodophenyl)propyl, N-(cysteinyl, glycyl, glycyl) 2-aminoethyl, (3',6',9'-triazanonoxy)ethyl, p-hydroxyphenylpropyl, and the carboxamide of N-nitrilotriacetic acid and 2-aminoethyl.

Alternatively, various cytotoxic agents may be employed, which are joined to the subject hydantoins by any convenient linking group, which does not significantly diminish the cytotoxic or antiproliferative activity of the compound. Compounds of interest include methotrexate, taxol, 5-fluorouracil, adriamycin, bleomycin, and the like.

The subject compounds can be prepared in accordance with conventional ways, varying the particular procedure based on the particular side groups. The preparation of hydantoins conveniently involves the use of an isocyanate and a substituted α-aminoacetonitrile. By appropriate choice of the isocyanate and the α-aminoacetonitrile, one may arrive at the final product in a single step. Alternatively, by employing various protective groups, which may be subsequently removed, or providing for substituents which become involved in the formation of the hydantoin or may provide for sites for further derivatization. Various procedures are described in EPO Publication Numbers 0 494 819 and 0 580 459. Also, a significant number of examples may be found in the subject experimental section.

The subject compositions find a variety of uses associated with prophylactic and therapeutic opportunities. By providing for substituents which allow for detection by x-rays, molecular resonance imaging, radioactivity, or the like, regions of a mammalian host, particularly humans, can be investigated, where the regions are associated with an androgenic receptor. Thus, cells or tissues associated with the androgenic receptors may be visualized, so as to identify neoplasms, benign tumors, mobile cells, etc. Thus, by having substituents which have radioactive atoms, heavy metals, heavy atoms such as iodine, or the like, one can visualize physiological structures associated with androgenic receptors.

In addition, the subject compounds have proliferative inhibitory capability in inhibiting the proliferation of cells having androgenic receptors and dependent upon signal transduction associated with the androgenic receptors. The subject compounds are found to have a high affinity for the androgenic receptors, demonstrating enhanced activity as compared to prior substituted hydantoins.

In addition, the subject hydantoins can be used as vehicles for transporting other cytotoxic agents to the androgen receptor comprising cells. Thus, while at the same time inhibiting androgenic activation, other pathways which inhibit proliferation may also be addressed. Thus, one can greatly enhance the therapeutic index of a known chemotherapeutic agent by directing the chemotherapeutic agent to specific sites in the host.

The subject compositions may be formulated in accordance with conventional ways for use in vivo. The subject compounds are found to be stable in human plasma at physiological temperatures. The subject compounds are found to have substantially greater cytostatic and cytotoxic effects in inhibiting cell growth for neoplastic cells, as compared to normal cells, i.e. having a high therapeutic index. The subject compositions are readily formulated in conventional carriers, such as saline, phosphate buffered saline, vegetable oils, ethanol, or other physiologically acceptable carrier.

The concentrations used for the subject compounds in diagnosis and therapy will be varied widely, depending upon the purpose of the compound, the patient being treated, the stage of the disease, whether the subject compounds are being used by themselves or in a combination therapy, the manner of administration, the responsiveness of the cancer cells to the drug, and the like. The particular dosage can be determined empirically. Other components of the formulation may include buffers, stabilizers, excipients, or the like. Depending upon the particular compound and its formulation, administration may be oral or parenteral, including intravascular, subcutaneous, intratumoral, intraperitoneally, etc.

The subject compounds may also be used in competitive assays for evaluating other compounds as to their cytotoxic or cytostatic effect. Thus, specific cell lines may be employed where the effect of an agent on the cytotoxic level of a subject compound may be determined in relation to the survival rate of the target cells. Also, in mixtures of cells containing neoplastic androgenic receptor containing cells the subject compounds can be used to eliminate the neoplastic cells in the presence of normal cells. Thus, in a variety of cultures, where androgenic receptor containing cells may be susceptible to becoming or are tumorous, by maintaining a cytoxic level of the subject compounds in the medium, the cells may be selectively killed.

The following examples are offered by way of illustration and not by way of limitation.

EXPERIMENTAL

The following compounds were prepared according to the general method described by Teutsch et al., J. Steroid Biochem. Molec. Biol. 1994; 1:111–119.

EXAMPLE 1

4-[3-(2'-(N-t-butoxycarbonyl)-aminoethyl)-4,4-dimethyl-5-imino-2-thioxo-1-imidazolidinyl]-2-trifluoromethyl-benzonitrile. (BP-136)

Crude 2-trifluoromethyl-4-isothiocyanato-benzonitrile (700 mg, 3.07 mmol) was dissolved in THF (6.0 mL). At room temperature, triethylamine (59 µL, 0.42 mmol) was added to the stirring solution followed by 2-(1',2'-ethyldiamino-N-t-butoxycarbonyl)-2-cyanopropane (682 mg, 3.00 mmol). The reaction was refluxed for 40 minutes under a $N_2$ atmosphere and then the solvent was removed under reduced pressure. The resulting brown residue was purified by silica gel chromatography ($CH_2Cl_2$; Acetone, gradient) and treated with activated carbon to yield 951 mg (68.1%) of light yellow powder.

mp:81° C.(dec); UV (MeOH):$\lambda_{max}$=234 nm ($\epsilon$=18841) and 260 nm ($\epsilon$=21454);

EXAMPLE 2

4-[4,4-dimethyl-3-(2',2'-dimethyl-1',3'-dioxolane-4'-methyl)-5-imino-2-thioxo-1-imidazolidinyl]-2-trifluoromethyl-benzonitrile. (BP-163)

BP-163 was prepared as described in Example 1 using the appropriate cyanoamine. Yield=63.3%.

UV (MeOH):$\lambda_{max}$=230 nm ($\epsilon$=23528), 244 nm ($\epsilon$=22733), and 258 nm ($\epsilon$=24590);

EXAMPLE 3

4-[4,4-dimethyl-5-imino-3-(2'-propenyl)-2-thioxo-1-imidazolidinyl]-2-trifluoromethyl-benzonitrile. (BP-208)

BP-208 was prepared by the same method described in Example 1 using the appropriate cyanoamine. Yield=67.3%.

EXAMPLE 4

4-[5-imino-2-thioxo-3-(2'-propynyl)-4,4-dimethyl-1-imidazolidinyl]-2-trifluoromethyl-benzonitrile (BP-211)

BP-211 was prepared as described in Example 1 using the appropriate cyanoanime. The compound was purified by chromatography ($CH_2Cl_2$/Acetone, 100%→50:50 gradient by 10% segments) and isolated as an orange oil. the product was not further characterized and dried as is in the subsequent hydrolysis step.

EXAMPLE 5

4-[4,4-dimethyl-3-(2'-{4"-imidazolyl}ethyl)-5-imino-2-thioxo-1-imidazolidinyl]-2-trifluoromethyl-benzonitrile. (BP-210)

BP-210 is prepared as described in Example 1 using the appropriate cyanoamine. The compound is purified by column chromatography and isolated by removal of volatiles as a pale yellow oil in good yield. It is used in the subsequent hydrolysis without further purification.

EXAMPLE 6

4-[4,4-dimethyl-5-imino-3-(2'-p-hydroxyphenylethyl)-2-thioxo-1-imidazolidinyl]-2 trifluoromethyl-benzonitrile. (BP-2 12 )

BP-212 is prepared as described in Example 1 using the appropriate cyanoamine. The crude product is then loaded into a silica gel column and is eluted with methylene chloride-acetone. The fractions containing products are combined and concentrated to dryness to give the product as a pale yellow solid. The product was used as is for further reactions.

EXAMPLE 7

4-[3-(2'-aminoethyl) 4,4-dimethyl-5-oxo-2-thioxo-1-imidazolidinyl]-2-trifluoromethyl-benzonitrile. (BP-138)

BP-136 (300 mg, 0.66 mmol) was dissolved in MeOH (3.5 m) and 2N HCI (0.65 mL, 1.30 mmol) with stirring at room temperature. The reaction mixture was refluxed for two hours, then the solvent was removed under reduced pressure, and the resulting solid was crystallized as the hydrochloride from isopropanol. Yield 204 mg (79.0%).

mp:>200° C.; UV (MeOH): $\lambda_{max}$=234 nm (18441) and 252 nm ($\epsilon$=20891)

EXAMPLE 8

4-[3-(2',3'-dihydroxypropyl)-4,4-dimethyl-5-oxo-2-thioxo-1-imidazolidinyl]-2-trifluoromethyl-benzonitrile. (BP-135)

BP-135 was prepared in the manner as described in Example 7 using the appropriate imine. The product was isolated by pouring the reaction mixture over a mixture of ice and water. The product was extracted with EtOAc, dried over $MgSO_4$ and the solvent removed under reduced pressure. BP-135 was purified by silica gel chromatography [$CH_2Cl_2$:Acetone, gradient] then treated with activated carbon to yield a hygroscopic amorphous solid. Yield=68.1%.

UV(MeOH):$\lambda_{max}$=234($\epsilon$=17480) and 254($\epsilon$=19963);

EXAMPLE 9

4-[4,4-dimethyl-5-oxo-3-(2'-propenyl)-2-thioxo-1-imidazolidinyl]-2-trifluoromethyl-benzonitrile. (BP-82)

BP-82 was prepared in the same manner as described in Example 7 using the appropriate imine. The product was isolated by pouring the reaction mixture over a mixture of ice and water. The product was extracted with EtOAc, dried over $MgSO_4$ and the solvent removed under reduced pressure. BP-82 was purified by treatment with activated carbon and crystallization from IPA. Yield=87.4%.

mp:146°–148° C.; UV (MeOH):$\lambda_{max}$=232 nm ($\epsilon$=18022) and 254 nm ($\epsilon$=21877)

EXAMPLE 10

4-[3-(2'-N-(t-butoxycarbonyl)-aminoethyl)-4,4-dimethyl-5-oxo-2-thioxo-1-imidazolidinyl]-2-trifluoromethyl-benzonitrile. (BP-137)

BP-137 was prepared in the same manner as described in Example 7 except the reaction was heated at 50° C. for eight hours. The resulting white crystalline precipitate was filtered off and washed with cold MeOH/$H_2O$ (50:50). Yield (87.1%).

mp:173°–175° C.; UV(MeOH):$\lambda_{max}$=234 nm ($\epsilon$=18573) and 256 nm ($\epsilon$=21038);

EXAMPLE 11

4-[4,4-dimethyl-3-[2',2'-dimethyl-1',3'-dioxolane-4'-methyl)-5-oxo-2-thioxo-1-imidazolidinyl]-2-trifluoromethyl-benzonitrile. (BP-134)

BP-134 was isolated as an impurity in the silica gel chromatographic purification of BP-163.

mp:50° C.(dec); UV (MeOH):$\lambda$hd max=234 nm ($\epsilon$=18765) and 254 ($\epsilon$=21499)

EXAMPLE 12

4-[4,4-dimethyl-3-(2'-propynyl)-5-oxo-2-thioxo-1-imidazolidinyl]-2-trifluoromethyl-benzonitrile. (BP-199)

BP-199 was prepared as described in Example 7. The product was isolated as colorless crystals from methylene chloride:hexane.

mp:120°–121° C.(dec);$\lambda_{max}$=206 nm ($\epsilon$=17,328), 232 ($\epsilon$=18,068), 252 ($\epsilon$=22,003).

EXAMPLE 13

4-[4,4-dimethyl-3-(2'-{4'-imidazolyl}ethyl)-5-oxo-2-thioxo-1-imidazolidinyl]-2-trifluoromethyl-benzonitrile. (BP-213)

BP-213 was prepared as described in Example 7. The crude product was purified by column chromatography and isolated as a colorless solid in high purity ($\geq$96%, HPLC).

UV:$\lambda_{max}$=234 nm ($\epsilon$=14,113.8), 254 ($\epsilon$=16,047.9).

EXAMPLE 14

4-[4,4-dimethyl-5-oxo-3-(2'-p-hydroxyphenylethyl)-2-thioxo-1-imidazolidinyl]-2-trifluoromethyl-benzonitrile. (BP-214)

BP-214 is prepared as described in Example 7. the crude product is crystallized form hexane/methylene chloride and isolated in good yield as colorless crystals.

EXAMPLE 15

4-[3-(2'-N-acetylaminoethyl)-4,4-dimethyl-5-oxo-2-thioxo-1-imidazolidinyl]-2-trifluoromethyl-benzonitrile. (BP-139)

The free amine of BP-138 (100 mg, 0.28 mmol) was dissolved in $(AcO)_2O$ (5.0 mL) and allowed to stir at room temperature for 30 minutes. The solvent was then removed under reduced pressure and the resulting off-white solid was purified by silica gel chromatography ($CH_2Cl_2$: Acetone, 95.5) to yield 102 mg (91.6%) of pure compound.

mp:77°–79° C.(dec);UV (MeOH):$\lambda_{max}$=234 ($\epsilon$=18,694), 254 (21,499)

EXAMPLE 16

4-[3-(2'-aminoethyl-N-(glycyl-N'-(2"-(triphenylmethyl thioacetyl)-glycine)))-4,4-dimethyl-5-oxo-2-thioxo-1-imidazolidinyl]-2-trifluoromethyl-benzonitrile. (BP-197)

DCC (1.1 mg, 5.35×10$^{-3}$ mmol) was added to a stirring solution of N-(2-triphenylmethylthioacetyl)-glycyl-glycine (2.0 mg, 4.46×10$^{-3}$ mmol) in THF (200 mL) at room temperature. The reaction was heated at 35° C. for two hours and then purified by preparative HPLC without further work up. Yield=50.2%.

EXAMPLE 17

4-[4,4-dimethyl-3-(4'-oxybutyl-O-glycyl-N-(2-(triphenylmethylthioacetyl)-glycine)))-5-oxo-2-thioxo-1-imidazolidinyl]-2-trifluoromethyl-benzonitrile. (BP-198)

To a stirred solution of 2-(triphenylmethylthioacetyl)-glycyl-glycine (2.0 mg, 4.46×10$^3$ mmol) in THF (200 mL) was added DCC (1.1 mg 5.35×10$^3$ mmol), 4-[4,4-dimethyl-3-(4'-hydroxybutyl)-5-oxo-2-thioxo-1-imidazolinyl]-2-trifluoromethyl-benzonitrile (2.1 mg, 5.35×10$^3$ mmol) [Synthesized as described by Teutsch et al., supra] and a crystal of DMAP at room temperature for 45 minutes. The reaction was purified by preparative HPLC without further work-up. Yield=56.8%

EXAMPLE 18

4-[3-(2-aminoethyl-N-(glycyl-N-'(2-thio)-glycine)))-4,4-dimethyl-5-oxo-2-thioxo-1-imidazolidinyl]-2-trifluoromethyl-benzonitrile. (BP-207)

$Bu_3SiH$ is added to a stirring solution of BP-198 in 10% TFA/$CH_2Cl_2$ and is purified by preparative HPLC without further workup. This product can now be used as a substrate for complexing with $^{99}$Tc by standard methods.

EXAMPLE 19

4-[4,4-dimethyl-3-4(oxybutyl-O-glycyl-N-(2-(thio)-glycine)))-5-oxo- 2-thioxo-2-imidazolidinyl]-2-trifluoromethyl-benzonitrile. (BP-209)

$Bu_3SiH$ is added to a stirring solution of BP-198 in 10% TFA/$CH_2Cl_2$ and is purified by preparative HPLC without further workup. This product can now be used as a substrate for complexing with $^{99}$Tc by standard methods.

EXAMPLE 20

The Gd-DTTA-HP-(NCO)$_2$ ($N^1$, $N^3$, -(bis-[3'-hydroxy-6'-[2"-isocyanatoethyl]pyridyl-2']methyl) diethylenetriamine triacetic acid (for a similar chelate see Tetrahedron 47, 357 (1991)) is taken up in DMF. In a separate flask BP-138 is dissolved in DMF. This solution is added to Gd-DTTA-HP-(NCO)$_2$ and stirred at 50° C. for 20 hours. The product is precipitated by Et$_2$O addition and purified by preparative HPLC. (BP-228)

EXAMPLE 21

The GdHDBHPI (tryptate) derivative is taken up in N-methyl pyrrolidone and BP-138 is added as a solid at once with stirring. The solution is stirred for 18 hours at ambient temperature. The product is isolated by precipitation in hexane and purified by preparative HPLC. (BP-229)

EXAMPLE 22

4-[4,4-dimethyl-3-(2'-propenyl-3'-iodo)-5-oxo-2-thioxo-1-imidazolidinyl]-2-trifluoromethyl-benzonitrile. (BP-215)

BP-82 is dissolved in cold (95%) phosphoric acid, to which phosphorous pentoxide is added. KI is added and the reaction is stirred and warmed to room temperature. After 2 hours, the reaction is poured onto ice water and extracted with methylene chloride. The combined organic layers are dried over MgSO$_4$. The product is purified by column chromatography and isolated as a colorless solid.

EXAMPLE 23

4-[4,4-dimethyl-3-(2'-{4"-imidazolyl 1-[2-$^{125}$I]}ethyl)-5-oxo-2-thioxo-1-imidazolidinyl]-2-trifluoromethyl-benzonitrile. (BP-216)

BP-216 is dissolved in methanol. Radioiodination is accomplished with chloramine-T and Na[$^{125}$I]I or Na[$^{131}$I]I or Na[$^{123}$I]I by known methods. [Hunter and Greenwood, Nature 1962; 194:495–496] TLC with autoradiography indicates 50–75% incorporation of the radionuclide.

EXAMPLE 24

4-[4,4-dimethyl-5-oxo-2-thioxo-3-(4'-trifluoromethanesulfonatylbutyl)-1-imidazolinyl]-2-trifluoromethyl-benzonitrile. (BP-217)

The substrate, compound RU-59063, described by Teutsch et al., supra, is dissolved in methylene chloride. Pyridine is added and the solution cooled to 0° C. Under nitrogen, triflic chloride is added slowly and the reaction warms to room temperature. The solution is cooled and pyridinium hydrochloride is filtered away. The product is isolated by removal of volatiles and stored under nitrogen at 0° C.

EXAMPLE 25

4-[4,4-dimethyl-3-(4'-$^{18}$Fluorobutyl)-5-oxo-2-thioxo-1-imidazolidinyl]-2-trifluoromethyl-benzonitrile. (BP-218)

a) Incorporation of $^{18}$F on BP-217 is accomplished by any of the known methods practiced at PET scanners. For example, $^{18}$F-CsF can be obtained from a neon target system. [Tewson and Welsh, J. Nuc. Med. 1978, 19:1339] Similarly the 2-$^{18}$F-ethyl can be prepared via the triflate derivative of RU-57073.

b) The $^{18}$F-labeled compound, BP-218 is also prepared with a no-carrier-added $^{18}$F using tetrabutyl ammonium ($^{18}$F) fluoride generated from [$^{18}$F]H$_2$O by the $^{18}$F reaction as described by Kilbourn and co-workers. [Kilbourn et al., Int. J. Appl. Radiat. Isot. 1984; 35:599] The product is purified by preparative reverse phase HPLC. The decay-corrected radiochemical yields range from 30–50%.

c) Direct fluorination of alcohols can also be accomplished by using diethylaminosulfur trifluoride.

[Tewson and Welch, J. Org. Chem. 1978, 43:1090] Thus, the hydroxybutyl, 4-[4,4-dimethyl-3-(4-hydroxybutyl)-5-oxo-2-thioxo-1-imidazolidinyl]-2-trifluoromethyl-benzonitrile, is treated with [$^{18}$F] Et$_2$NSF$_3$ (generated from a neon target) in THF at –78° C. After slowly warming to room temperature, the volatiles are removed and the product is purified by column chromatography.

EXAMPLE 26

7-{imidazolidinyl-5",5"-dimethyl-4"-oxo-3"-[4"'-cyano-3"'-trifluoromethylphenyl-imidazolidinyl]-2"-thioxo-1"-ethylcarbamoxy}paclitaxel. [BP-196]

A round bottom flask charged with paclitaxel (60 mg, 0.07 mmol), imidazole (90 mg, 1.32 mmol) and a magnetic stir bar was placed under a N$_2$ atmosphere. CH$_2$Cl$_2$ (1.5 mL) was added and the solution was stirred at room temperature. To the solution was added portionwise a solution of 1.0M ClSiEt$_3$ in THF (5×100 μL, 0.5 mmol). The progress of the reaction was monitored by HPLC. Upon completion, the 2'-(triethylsiloxy)paclitaxel was purified by preparative HPLC yielding 51.3 mg (75%). Purity by HPLC 97%. Proton NMR of the product matched values given in the literature [Chandhary et al., J. Org. Chem. 1993; 58(15) :3798–3799]

A round bottom flask charged with 2'-(triethylsiloxy pacli-taxel (30 mg, 0.03 mmol) and p-nitrophenylchloroformate (310 mg, 1.50 mmol) and a magnetic stir bar was placed under a N$_2$ atmosphere. A solution of pyridine (200 μL, 0.247 mmol) in CH$_3$CN (1.0 mL) was added and the mixture stirred at room temperature for 30 minutes. The product 2'-(triethylsiloxy), 7-(p-nitrophenylcarbonoxy)paclitaxel was purified by preparative HPLC yielding 24.2 mg (69%). Purity by HPLC was 96%.

To a round bottom flask charged with 2'-(triethylsiloxy), 7-(p-nitrophenyl-carbonoxy)paclitaxel (28.0 mg, 0.014 mmol), 4-[3-(2-aminoethyl-4',4'-dimethyl-5-oxo-2-thioxo-1-imidazolidinyl]-2-(trifluoromethyl)-benzonitrile (2×8.0 mg, 0.44 mmol) and a magnetic stir bar was added CH$_2$Cl$_2$ (300 μL). The solution was stirred at room temperature for 4 hours and the product, 2'-(triethylsiloxy)-7-{5",5"-dimethyl-4"-oxo-3"-[4"'-cyano-3"'-(trifluoromethyl)phenyl-1-imidazolidinyl]-2-"thioxo-1"-ethylcarbamoxy}paclitaxel, was purified by preparative HPLC yielding 8.2 mg (85%). Purity by HPLC 97%.

To a round bottom flask charged with 2'-(triethylsiloxy)-7-{5",5"-dimethyl-4"-oxo-3"-[4"'-cyano-3"'-(trifluoromethyl)phenyl-1-imidazolidinyl]-2-"thioxo-1"-ethylcarbamoxy}paclitaxel (5.0 mg, 0,004 mmol) and equipped with a stir bar was added formic acid (250 mL). The solution as stirred at room temperature for 15 minutes and the volatiles removed under vacuum. 7-{5",5"-dimethyl-4"-oxo-3"-[4"'-cyano-3"'-(trifluoromethyl)phenyl-1-imidazolidinyl]-2-"thioxo-1"-ethylcarbamoxy}paclitaxel was purified by preparative HPLC yielding 4.6 mg (>99%). Purity by HPLC 99%.

Testing:

All compounds were tested for stability by incubation in human plasma at 38° C. for three hours and subsequent analysis by high pressure liquid chromatography. All compounds tested were found to be stable under these conditions.

All compounds were screened on a panel of normal and cancer human cell lines, including human prostate cancer cell lines, PC-3, DU-145, and LnCAP. The purpose of this experiment was to assess cell growth inhibition by measuring cytotoxicity and cytostatic effects.

Cells ($10^4$/well) were plated on 96 well plates with the following controls: no cells and toxic control ($1 \times 10^{-3}$ M sodium dodecyl sulfate (SDS). The drug was diluted in ethanol and added directly to the wells. Plates were incubated at 37° C. under 5% carbon dioxide in sterile air, in a humidified incubator for 72 hours. A solution (50 µl of 2,3-bis-(methoxy-4-nitro-5-sulfophenyl)-5-[(phenylamino) carbonyl]-2H-tetrazolium hydroxide (XTT), 1 mg/mL) in phosphate buffered saline (PBS, 100 mM) was added to each well. In the presence of viable cells, this colorless clear solution is enzymatically transformed to give a pink coloration, read at 450 nm using a microplate reader (Molecular Devices Thermomax). The inhibition of cell growth was measured by hemocytometer, counting cell viability. (Table I)

The results of compounds hitherto investigated are shown in Tables I and II. While the cytostatic effect of BP-82 is demonstrated in PC-3 human cell line (Table II), the growth inhibition (which reflects primarily cytotoxicity and may obscure the cytostatic property) is shown for compounds BP-196 and BP-199.

It is not certain whether the cytoxicity of BP-196 can be ascribed to the taxol moiety. The toxicity of this compound vis-a-vis normal cells is also quite high.

On the other hand, it appears that such targeting does occur with BP-199 which is most cytotoxic in the human prostate cancer lines containing at least some androgen receptors, but has low cytotoxicity in a variety of other human transformed and normal cells.

The androgenic and anti-androgenic activity of the current and novel compounds was tested in a specific assay described by Fuhrman et al. [J. Steroid Biochem. Molec. Biol. 1992; 42: 787–793]. This assay uses CV-1 cells derived from monkeys transfected with human androgen receptors. (Table III and IV).

TABLE I

Inhibition of Cell Proliferation at 72 hours:
Cytotoxic Effects of the Selected Novel Anti-Androgens.

| Cell Line | Tumor | IC$_{50}$ [M] BP-82 | BP-196 | BP-199 |
|---|---|---|---|---|
| DU-145 | Human Prostate (receptor poor) | $1.39 \times 10^{-5}$ | $8.67 \times 10^{-7}$ | $8.51 \times 10^{-5}$ |
| Ln CAP | Human Prostate (with androgen receptors) | $6.60 \times 10^{-5}$ | $1.31 \times 10^{-7}$ | $8.20 \times 10^{-7}$ |
| PC-3 | Human Prostate (few androgen receptors) | $3.15 \times 10^{-5}$ | $3.72 \times 10^{-8}$ | $1.32 \times 10^{-7}$ |
| MCF-7 | Human Breast | $5.00 \times 10^{-5}$ | $9.89 \times 10^{-7}$ | $1.00 \times 10^{-4}$ |
| MCF-7/ADR | Human Breast (adriamycin resistant) | $1.51 \times 10^{-5}$ | $1.00 \times 10^{-5}$ | $1.00 \times 10^{-5}$ |
| Ovcar 3 | Human Ovary | $9.65 \times 10^{-5}$ | $5.00 \times 10^{-8}$ | $>10^{-4}$ |
| Molt-4 | Human T-cell Leukemia | $4.88 \times 10^{-5}$ | $1.47 \times 10^{-7}$ | $>10^{-4}$ |
| L-1210 | Mouse Leukemia Normal | $2.50 \times 10^{-5}$ | $9.70 \times 10^{-7}$ | $1.10 \times 10^{-5}$ |
| NH DF | Dermal Fibroblast (human) | $9.17 \times 10^{-5}$ | $1.07 \times 10^{-7}$ | $>10^{-4}$ |
| HLF-1 | Normal Lung Diploid (human) | $3.90 \times 10^{-5}$ | $8.06 \times 10^{-6}$ | $>10^{-4}$ |
| CHO | Chinese Hamster Ovary | $3.45 \times 10^{-5}$ | $8.76 \times 10^{-6}$ | $1.28 \times 10^{-5}$ |

TABLE II

Relative Growth Inhibition*
Hydantoin Derivatives at $10^{-5}$ M after 6 days.

| Compound | No. of cells remaining expressed as a % of control | Observation |
|---|---|---|
| BP-82 | ≈70% | growth reduction only |
| BP-196 | ≈100% | cytotoxic cell death |
| BP-199 | ≈50% | growth reduction only |
| BP-213 | ≈40% | some cytotoxicity and growth reduction |
| BP-231 | ≈30% | growth reduction only |

*Cell density $10^4$/well

TABLE III

Anti-androgenic potency (IC$_{50}$) of current and novel anti-androgens.
Transactivation assay in CV1-3.9.2 cells;
Stimulation with 0.1 nM testosterone)

| COMPOUND | IC$_{50}$[nM] |
|---|---|
| Cyproterone Acetate | 11 |
| RU59063* | 23 |
| Hydroxyflutamide | 35 |
| Casodex | 180 |
| BP134 | 21 |
| BP135 | 158 |
| BP136 | 200 |
| BP137 | 20 |
| BP138 | 139 |
| BP139 | 239 |
| BP199 | 15 |
| BP82 | ≈6.5 |
| BP163 | 217 |

*Described by Teutsch, (Ref. 1)

TABLE IV

Androgen Activity of Anti-Androgens in CVI-3.9.2 Cells

| Test Compounds* | CAT Activity [cpm] |
|---|---|
| EtOH+ | 2250 |
| R1881 (0.1nM)+ | 5400 |
| R1881 (1.0nM)+ | 5600 |
| R1881 (10nM)+ | 6700 |
| RU59063 | 2600 |
| BP134 | 1600 |
| BP135 | 1900 |
| BP136 | 1800 |
| BP137 | 2000 |
| BP138 | 1600 |
| BP139 | 1500 |
| BP82 | 1300 |
| BP163 | 2100 |

*(Except as indicated, all compounds were tested at 1 µM)
+Controls

It is evident from the above results, that the subject compounds provide for a variety of advantages in directing a variety of agents to androgenic receptors of cells. Substantial therapeutic index is available between tumor cells and normal cells. The compounds are stable and can be readily formulated in a variety of ways. In addition, the subject compounds can be used as vehicles for bringing to tumor cells having androgenic receptors, cytotoxic agents, contrast agents, radioactive atoms, and the like. In this way, tumors having androgenic receptors may be visualized, as well as treated therapeutically.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A compound selected from the group consisting of:
   (a) 4-[3'-(2"-propenyl)-4',4'-dimethyl-5'-oxo-2'-thioxo-1'-imidazolidinyl]-2-trifluoromethyl-benzonitrile;
   (b) 7{5"',5"-dimethyl-4"-oxo-3"-[4'"-cyano-3'"-trifluoromethylphenyl-1'-imidazolidinyl]-2"-thioxo-1"-ethylcarbamoxy}paclitaxel;
   (c) 4-[3'-(2"-propynyl)-4',4'-dimethyl-5'-oxo-2'-thioxo-1'-imidazolidinyl]-2-trifluoromethyl-benzonitrile;
   (d) 4-[3'-(2"-{4'"-imidazolyl}ethyl)-4',4'-dimethyl-5'-oxo-2'-thioxo-1'-imidazolidinyl]-2-trifluoromethyl-benzonitrile;
   (e) 4-[3'-{2"-N-(ρ-hydroxy phenethyl) amidoethyl}-4',4'-dimethyl-5'-oxo-2'-thioxo-1'-imidazolidinyl]-2-trifluoromethyl-benzonitrile;
   (f) 4-[3'-(2",2"-dimethyl-1",3"-dioxolane-4"-methyl)-4',4'-dimethyl-5'-oxo-2'-thioxo-1'-imidazolidinyl]-2-trifluoromethyl-benzonitrile;
   (g) 4-[3'-(2",3"-dihydroxypropyl)-4',4'-dimethyl-5'-oxo-2'-thioxo-1'-imidazolidinyl]-2-trifluoromethyl-benzonitrile;
   (h) 4-[3'-(2"-N-(t-butoxycarbonyl)-aminoethyl)-4',4'-dimethyl-5'-imino-2'-thioxo-1'-imidazolidinyl]-2-trifluoromethyl-benzonitrile;
   (i) 4-[3'-(2"-N-(t-butoxycarbonyl)-aminoethyl)-4',4'-dimethyl-5'-oxo-2'-thioxo-1'-imidazolidinyl]-2-trifluoromethyl-benzonitrile;
   (j) 4-[3'-(2"-aminoethyl)-4',4'-dimethyl-5'-oxo-2'-thioxo-1'-imidazolidinyl]-2-trifluoromethyl-benzonitrile;
   (k) 4-[3'-(2"-N-acetylaminoethyl)-4',4'-dimethyl-5'-oxo-2'-thioxo-1'-imidazolidinyl]-2-trifluoromethyl-benzonitrile;
   (l) 4-[3'-(2",2"-dimethyl-1",3"-dioxolane-4"-methyl)-4',4'-dimethyl-5'-imino-2'-thioxo-1'-imidazolidinyl]-2-trifluoromethyl-benzonitrile;
   (m) 4-[3'-(4"-fluorobutyl)-4',4'-dimethyl-5'-oxo-2'-thioxo-1'-imidazolidinyl]-2-trifluoromethyl-benzonitrile;
   (n) 4-[3'-trans-(2"-propenyl-3"-iodo)-4',4'-dimethyl-5'-oxo-2'-thioxo-1'-imidazolidinyl]-2-trifluoromethyl-benzonitrile;
   (o) 4-[3'-gem-(2"-propenyl-2"-iodo)-4',4'-dimethyl-5'-oxo-2'-thioxo-1'-imidazolidinyl]-2-trifluoromethyl-benzonitrile;
   (p) 4-[3'-cis-(2"-propenyl-3"-iodo)-4',4'-dimethyl-5'-oxo-2'-thioxo-1'-imidazolidinyl]-2-trifluoromethyl-benzonitrile;
   (q) 4-[3'-methylcyclopropyl)-4',4'-dimethyl-5'-oxo-2'-thioxo-1'-imidazolidinyl]-2-trifluoromethyl-benzonitrile;
   (r) 4-[3'-cis-(2"-propenyl-3"-bromo)-4',4'-dimethyl-5'-oxo-2'-thioxo-1'-imidazolidinyl]-2-trifluoromethyl-benzonitrile;
   (s) 4-[3'-trans-(2"-propenyl-3"-chloro)-4',4'-dimethyl-5'-oxo-2'-thioxo-1'-imidazolidinyl]-2-trifluoromethyl-benzonitrile; and
   (t) 4-[3'-trans-(propanyl-3"-carboranyl)-4',4'-dimethyl-5'-oxo-2'-thioxo-1'-imidazolidinyl]-2-trifluoromethyl-benzonitrile.

2. A compound according to claim 1, wherein said 4-[3'-(4"-fluorobutyl)-4',4'-dimethyl-5'-oxo-2'-thioxo-1'-imidazolidinyl]-2-trifluoromethyl-benzonitrile comprises $^{18}F$ or $^{19}F$.

3. A compound according to claim 1 which is 4-[3'-trans-(2"-propenyl-3"-iodo)-4',4'-dimethyl-5'-oxo-2'-thioxo-1'-imidazolidinyl]-2-trifluoromethyl-benzonitrile where iodo is radioactively labeled iodine.

4. A compound according to claim 1 which is 4-[3'-gem-(2"-propenyl-2"-iodo)-4',4'-dimethyl-5'-oxo-2'-thioxo-1'-imidazolidinyl]-2-trifluoromethyl-benzonitrile where iodo is radioactively labeled iodine.

5. A compound according to claim 1 which is 4-[3'-cis-(2"-propenyl-3"-iodo)-4',4'-dimethyl-5'-oxo-2'-thioxo-1'-imidazolidinyl]-2-trifluoromethyl-benzonitrile where iodo is radioactively labeled iodine.

6. In a method for specifically directing an agent to cells comprising an androgenic receptor by adding said agent to a mammalian host comprising said cells, the improvement which comprises:

said agent being a compound according to claim 1.

7. A method according to claim 6, wherein said compound comprises a radioactive atom or heavy atom.

* * * * *